(12) United States Patent
Menassa

(10) Patent No.: US 9,498,407 B2
(45) Date of Patent: Nov. 22, 2016

(54) NEEDLELESS INJECTOR ACCESSORIES

(75) Inventor: Karim Menassa, Montreal (CA)

(73) Assignee: Medical International Technologies (MIT Canada) Inc., Ville St. Laurent, Quebec (CA)

(*) Notice: Subject to any disclaimer, the term of this patent is extended or adjusted under 35 U.S.C. 154(b) by 0 days.

(21) Appl. No.: 13/261,020

(22) PCT Filed: May 28, 2010

(86) PCT No.: PCT/CA2010/000820
§ 371 (c)(1),
(2), (4) Date: Nov. 17, 2011

(87) PCT Pub. No.: WO2010/135840
PCT Pub. Date: Dec. 2, 2010

(65) Prior Publication Data
US 2012/0059315 A1     Mar. 8, 2012

Related U.S. Application Data

(60) Provisional application No. 61/213,302, filed on May 28, 2009.

(51) Int. Cl.
*A61M 5/30* (2006.01)
*A61J 1/20* (2006.01)

(52) U.S. Cl.
CPC .................................. *A61J 1/2096* (2013.01)

(58) Field of Classification Search
USPC ...................................................... 604/68–72
See application file for complete search history.

(56) References Cited

U.S. PATENT DOCUMENTS

| 4,342,310 A * | 8/1982 | Lindmayer et al. | 604/70 |
| 7,357,781 B2 * | 4/2008 | Menassa | 604/70 |
| 2005/0085767 A1 * | 4/2005 | Menassa | 604/68 |

* cited by examiner

*Primary Examiner* — Nicholas Lucchesi
*Assistant Examiner* — Niyati D Shah
(74) *Attorney, Agent, or Firm* — George A. Seaby

(57) ABSTRACT

A disposable nozzle for use on the discharge end of the barrel of a needleless injector is threaded onto the front end of a holder mounted in the barrel. A resilient detent extending outwardly at an acute angle from the inner wall of a recess in the rear end of the nozzle repeatedly enters and exits notches in a sleeve on the holder when the nozzle is mounted on the holder providing an audible signal that the nozzle has not been used. Reverse rotation of the nozzle during removal from the holder results in breaking of the detent. Thus, mounting of a used nozzle on the holder would not be accompanied by a signal that the nozzle is unused.

7 Claims, 9 Drawing Sheets

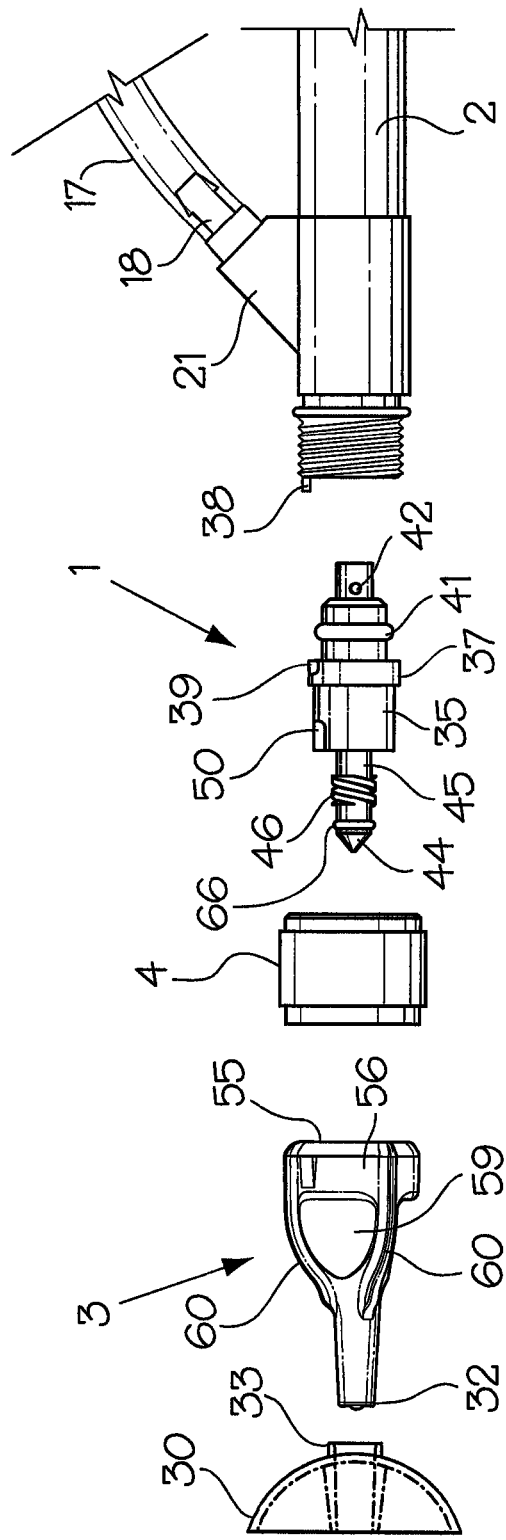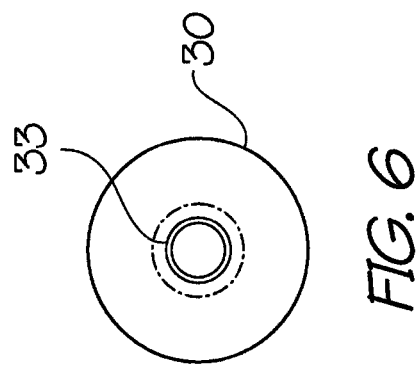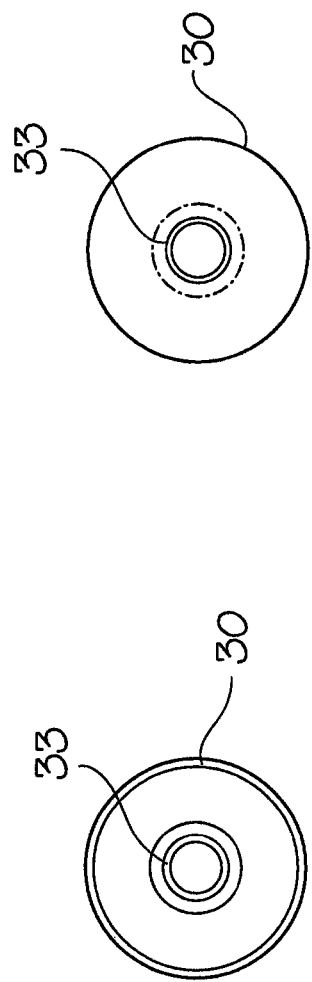

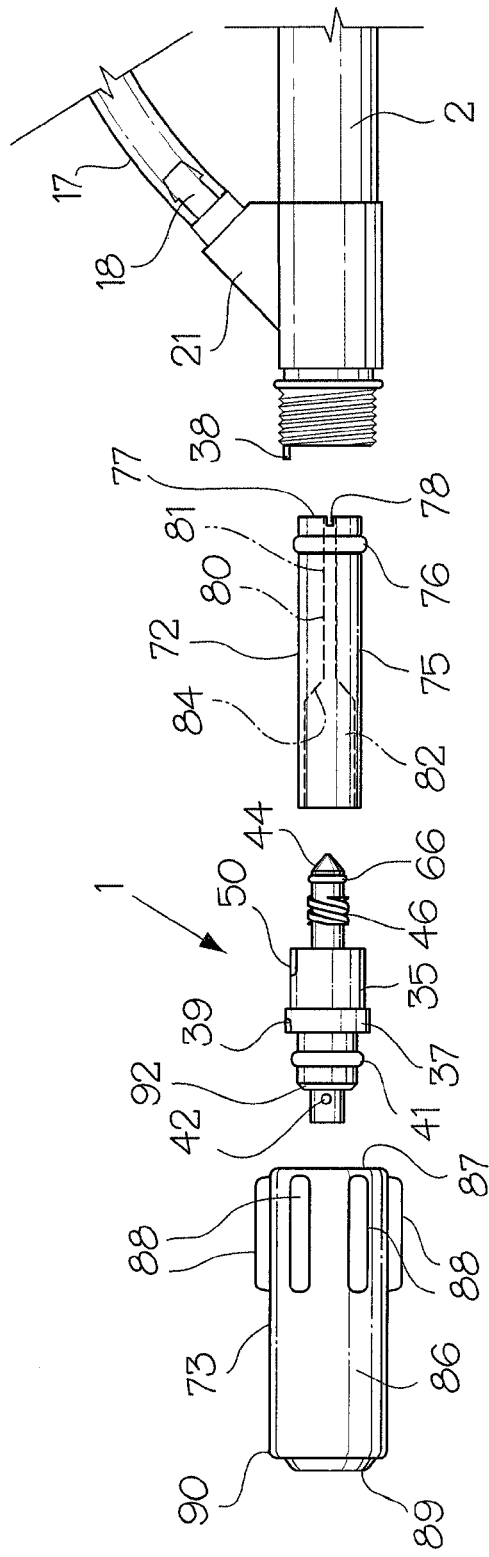

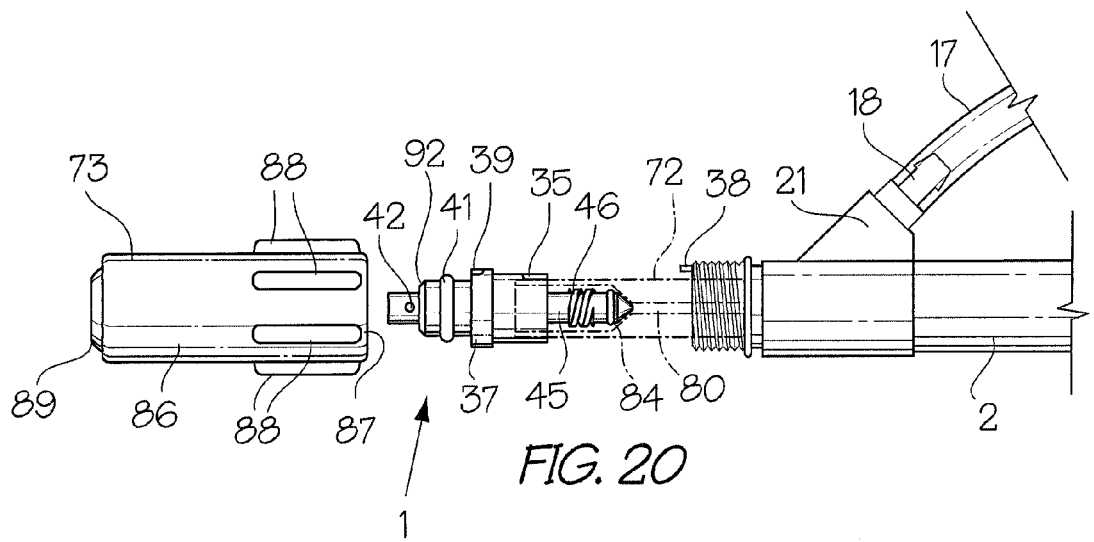
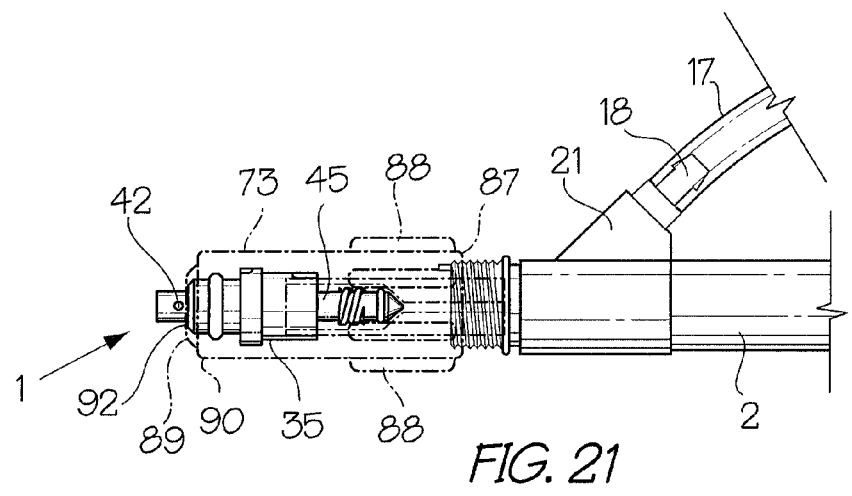

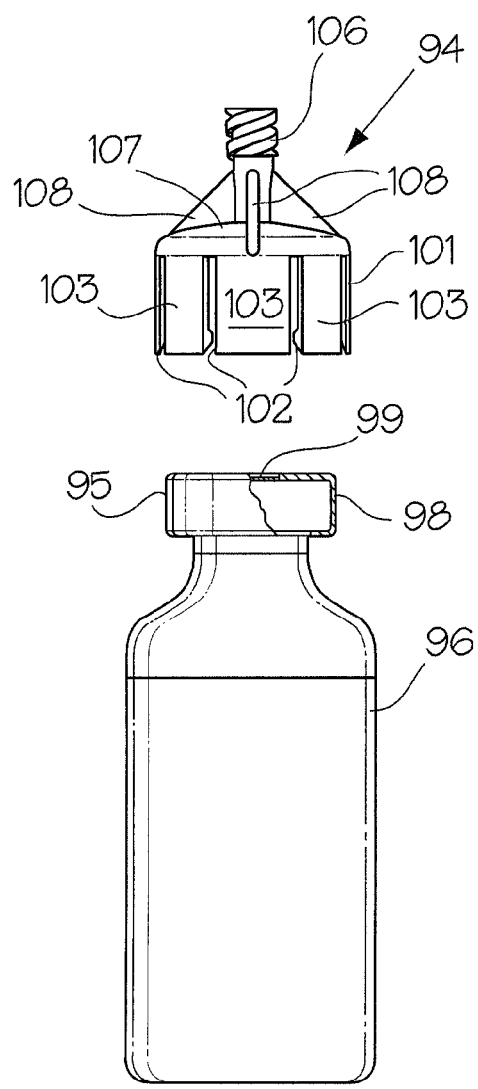
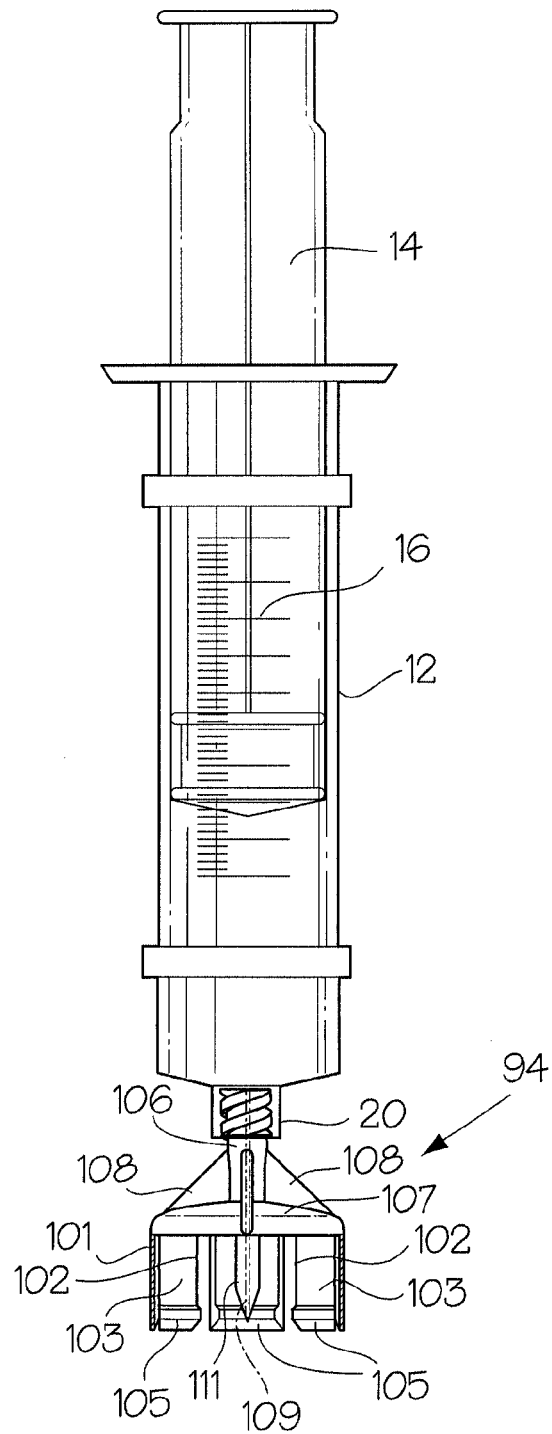
FIG. 22
FIG. 23

NEEDLELESS INJECTOR ACCESSORIES

This application claims the benefit of U.S. Provisional Application No. 61/213,302, filed on May 28, 2009, which is incorporated herein by reference in its entirety.

FIELD OF THE INVENTION

This invention relates to accessories for needleless injectors.

BACKGROUND OF THE INVENTION

In accordance with one aspect, the invention relates to a disposable nozzle for use on a needleless injector of the type disclosed by the inventor's U.S. Pat. No. 7,357,781, issued Apr. 15, 2008. As described in the abstract, the patented injector includes a barrel for receiving an injectable liquid, a nozzle closing one end of the barrel containing an injection orifice, and a plunger and piston combination in the barrel. A valve admits gas under pressure into the barrel behind the piston. A trigger opens the valve to cause the piston to move against the plunger, and a magnet retains the piston in a rest position in the barrel until acted upon by the gas under sufficient pressure to cause the piston and plunger to move to an extended, discharge position. While the disposable nozzle is intended for use on the patented injector, it also can be used on other injectors of the same type, i.e. injectors including a barrel and a plunger for discharging a liquid through a valve and nozzle in one end of the barrel.

In the patented device, the nozzle is retained in the outlet end of the barrel by an internally threaded cap. Thus, in order to replace the nozzle, it is necessary to unscrew the cap, remove the nozzle, place a new nozzle in the barrel and replace the cap.

SUMMARY OF THE INVENTION

In accordance with the present invention, the nozzle is a disposable nozzle, which is held in the injector by a nozzle holder. The nozzle holder is mounted in the discharge end of the barrel and held in position by an internally threaded cap. The disposable nozzle is mounted on an outer end of the holder, and can be removed simply by rotating the nozzle after an injection has occurred.

More specifically, the present invention provides a nozzle assembly for use on the discharge end of the barrel of a needleless injector comprising a holder for mounting in the discharge end of the barrel and a disposable nozzle for mounting on the holder, the holder including:
  a tubular holder body having a central, longitudinally extending passage therethrough permitting the passage of fluid from the injector barrel to the disposable nozzle;
  an externally threaded holder nozzle at the front, discharge end of the holder body;
  a cylindrical sleeve on the holder body around the rear end of said externally threaded holder nozzle; and
  at least one first notch in a front, free end of the sleeve;
the disposable nozzle including:
  a tubular, internally threaded nozzle body having external threads for mounting the disposable nozzle on the front end of the holder;
  an annular recess with inner and outer walls in a rear end of the nozzle body for receiving the sleeve of the holder when the disposable nozzle is mounted on the holder, and
  a resilient, frangible detent extending outwardly at an acute angle from said inner wall of said recess into the path of travel of the holder sleeve when the disposable nozzle is being threaded onto the holder,
whereby, when the disposable nozzle is rotated in one direction while being threaded onto the holder, the detent is deflected towards said inner wall of the recess, and when the disposable nozzle is fully on the holder, the detent extends into the at least one first notch and reverse rotation of the disposable nozzle results in breaking of the detent.

BRIEF DESCRIPTION OF THE DRAWINGS

The nozzle and holder are described in greater detail with reference to the accompanying drawings, wherein:

FIG. 4 is an exploded side view of the discharge end of the injector of FIGS. 1 to 3; the holder and the disposable nozzle;

FIGS. 5 and 6 are end views of a spacer used on the nozzle of the present invention;

FIG. 15 is an exploded view of the discharge end of the injector of FIG. 1, the holder and a device for cleaning the holder.

FIGS. 16 and 17 are end views of a tube used in the cleaning device of FIG. 15;

FIGS. 18 and 19 are end views of a cap used in the cleaning device of FIG. 15;

FIG. 20 is an exploded side view of the cleaning device mounted on the injector;

FIG. 21 is a side view of the cleaning device being mounted on the injector;

FIG. 22 is an exploded side view of a medicine bottle and an adapter for connecting a syringe to the bottle; and FIG. 23 is a partly sectioned side view of a syringe and the adapter of FIG. 22.

DETAILED DESCRIPTION OF THE INVENTION

Figure 1:
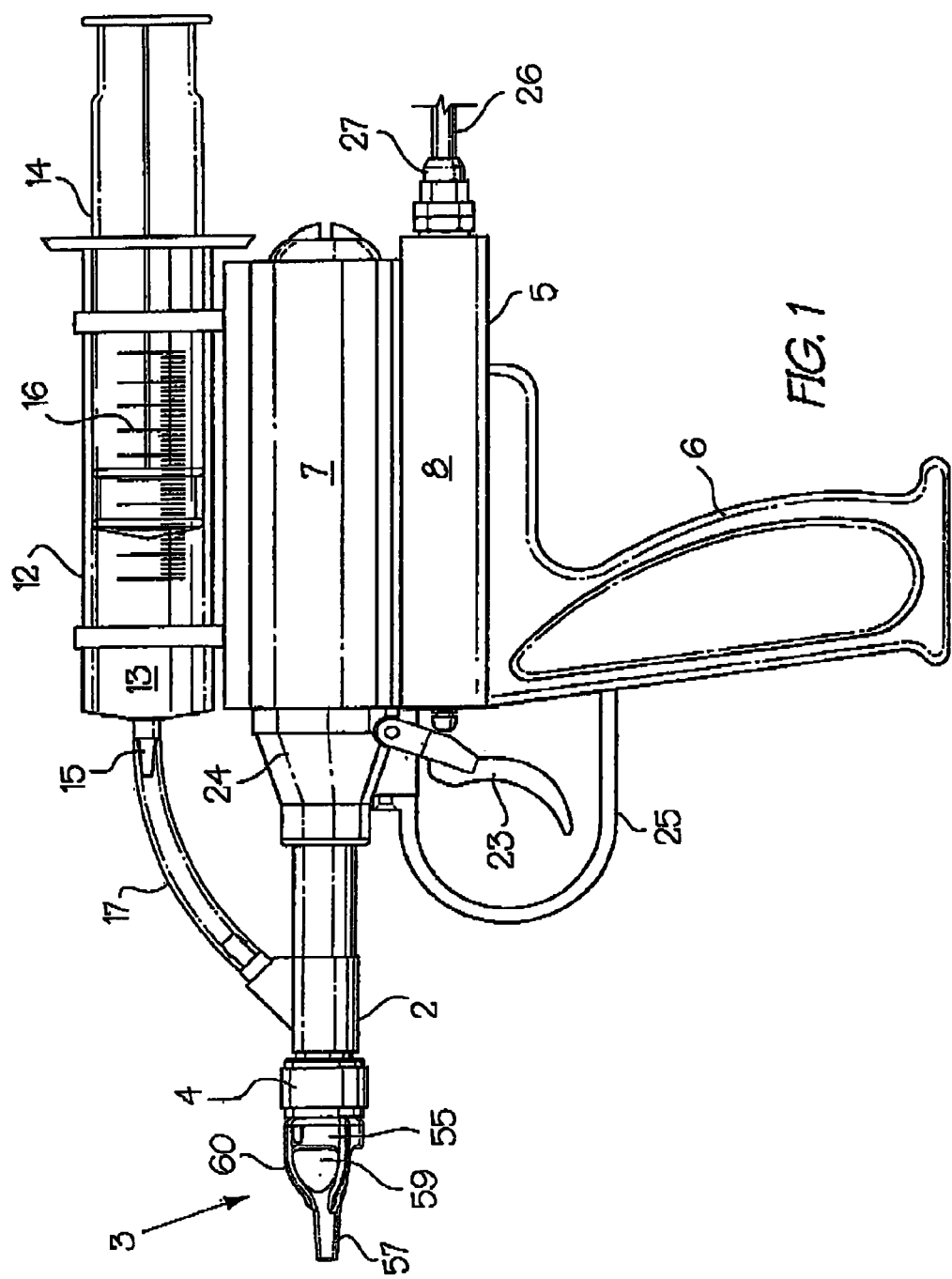
FIG. 1 is a side view of a needleless injector with a nozzle in accordance with the present invention mounted thereon.
Figure 2:
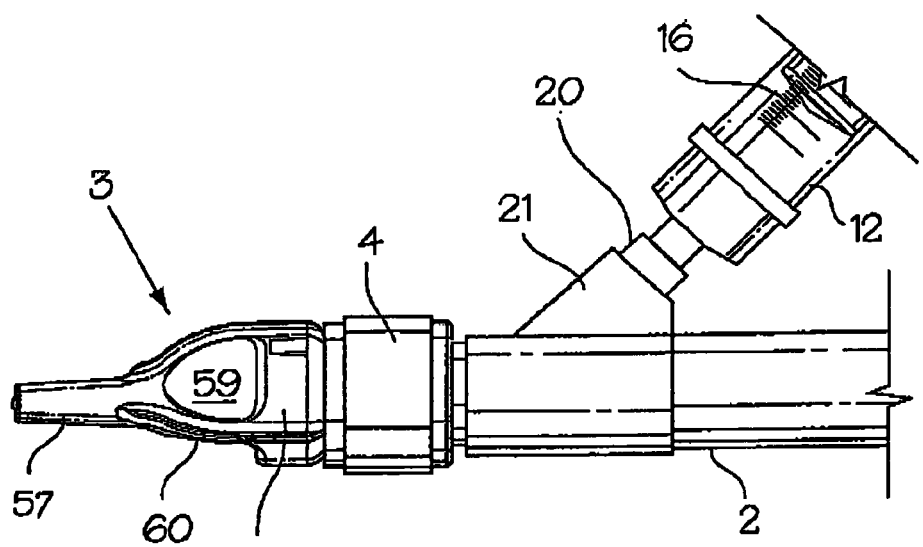
FIG. 2 is a side view of the discharge end of the injector of FIG. 1 on a larger scale.
Figure 3:
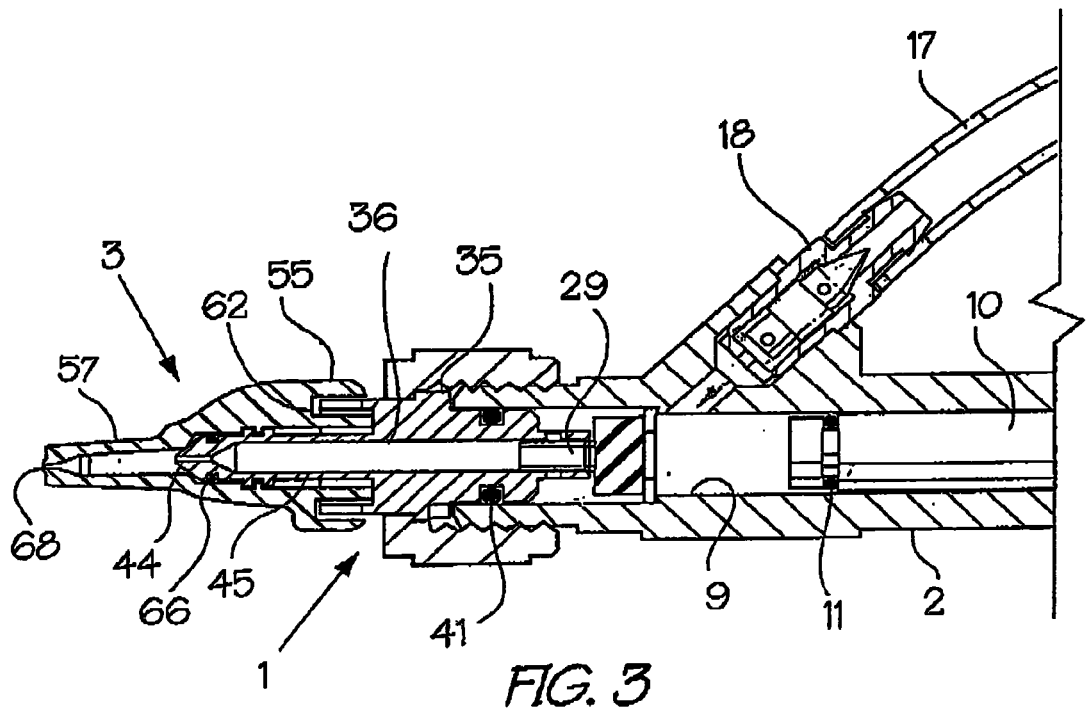
FIG. 3 is a longitudinal sectional view of the discharge end of the injector of FIGS. 1 and 2 showing a holder and the nozzle.
Figure 7:
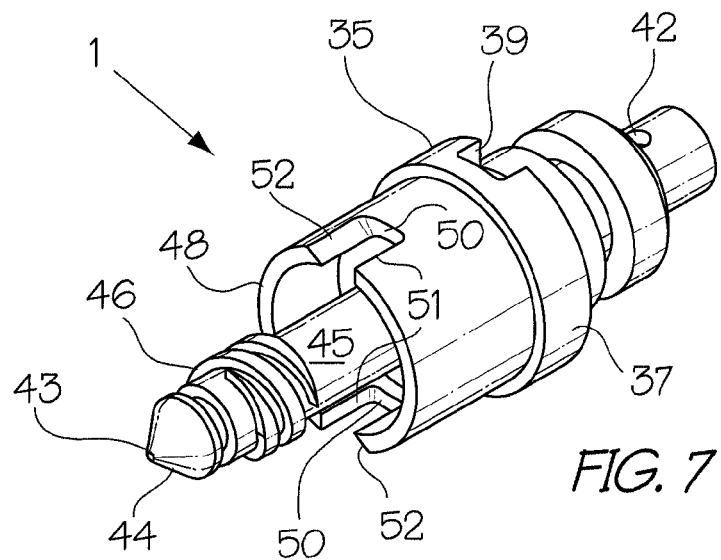
FIG. 7 is an isometric view of the holder.
Figure 8:
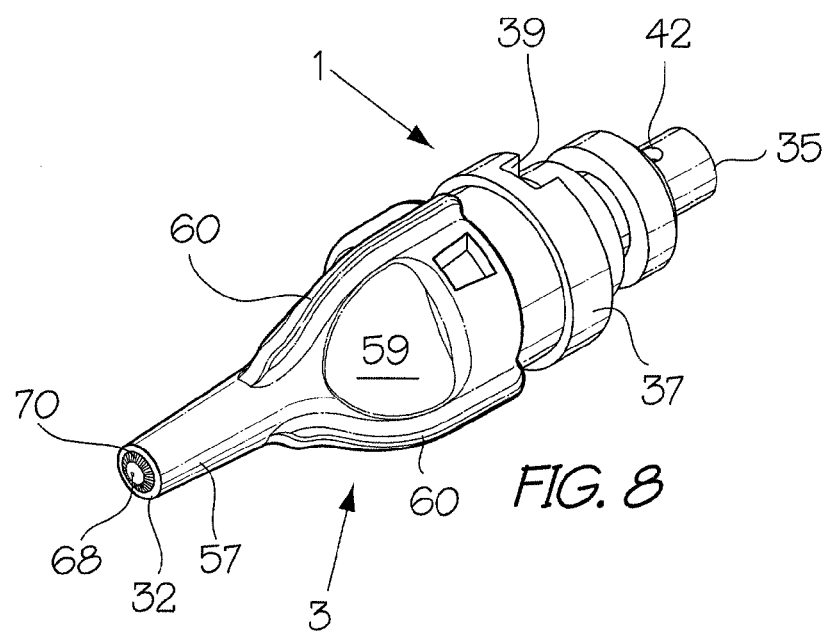
FIG. 8 is an isometric view of the assembled holder and the disposable nozzle.
Figure 9:
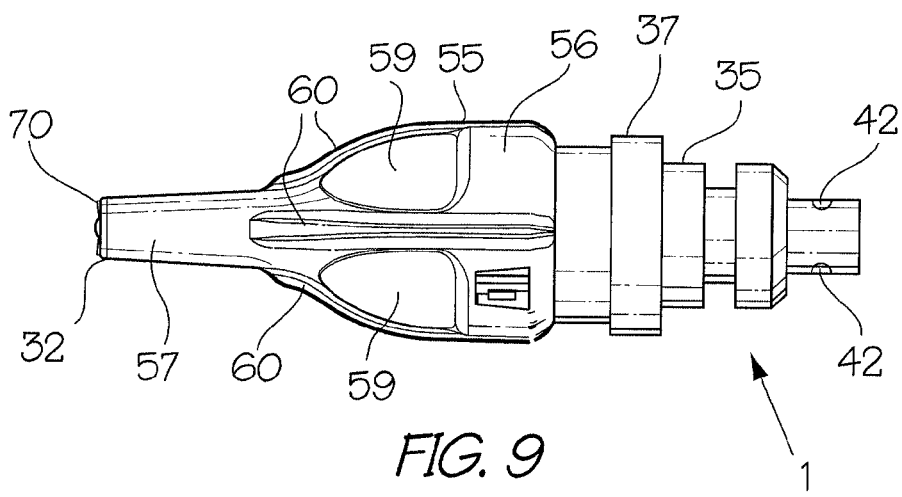
FIG. 9 is a side view of the assembled holder and nozzle.
Figure 10:
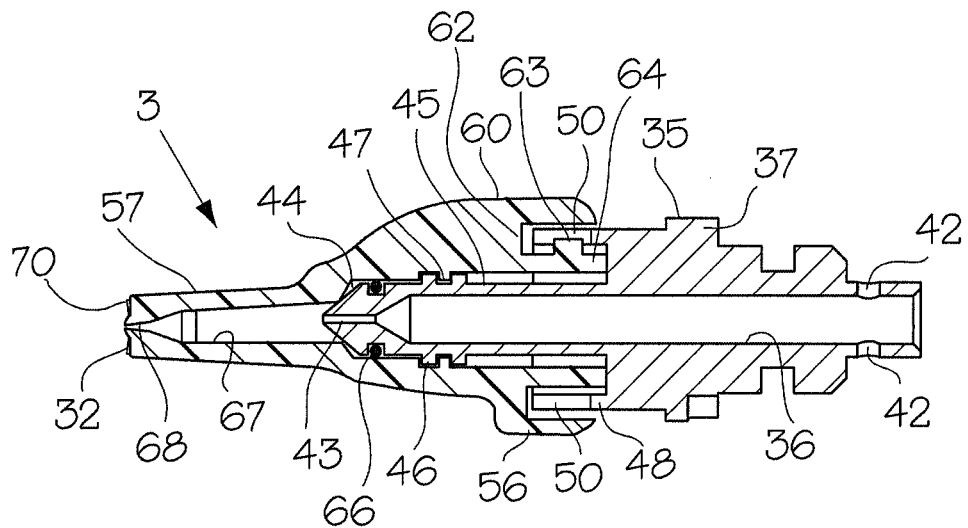
FIG. 10 is a longitudinal sectional view of the holder and nozzle of FIGS. 8 and 9.
Figure 11:
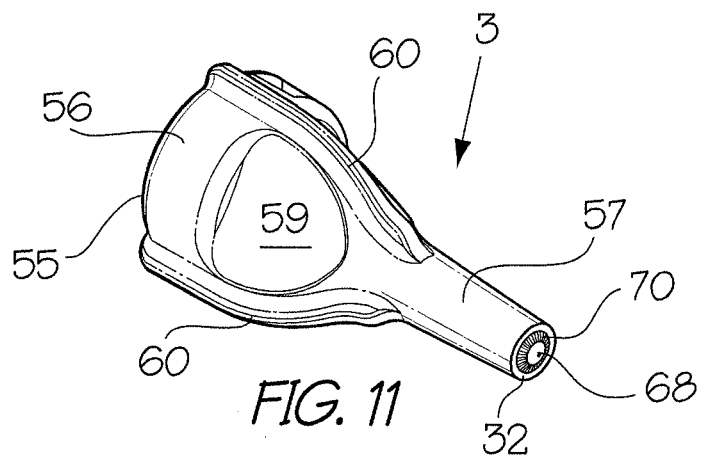
FIG. 11 is an isometric view of the nozzle.

With reference to FIGS. 1 to 4, a holder used in the nozzle assembly of the present invention which is indicated generally at 1 is mounted in the discharge end of an injector barrel 2, and a nozzle indicated generally at 3 is releasably connected to the holder 1. The holder 1 is held in the externally threaded front end of the injector barrel 2 by an internally threaded cylindrical cap 4 with an inwardly extruding, annular flange on one end thereof. The injector 2 is in the shape of a pistol and includes a body 5 with a handle 6 extending downwardly therefrom. The body 1 includes upper and lower cylinders 7 and 8, respectively which, as shown in U.S. Pat. No. 7,357,781, contain most of the elements of the injector. The cylinder 7 defines one end of the barrel 2. The barrel 2 contains a passage 9 carrying a piston (not shown), and a plunger 10. The plunger 10 is sealed in the barrel 2 by an O-ring 11. Rearward movement of the plunger 10 creates a partial vacuum in the passage 9 in front of the plunger to draw medicine into the passage from a syringe 12. The syringe 12 is a conventional plastic syringe including a barrel 13 with a plunger 14 slidable therein for discharging liquid through a narrow diameter nozzle 15. A scale 16 on the side of the barrel 13 indicates the dosage. The syringe can be replaced by a medicine bag or bottle. Liquid is discharged from the nozzle 15 through a plastic tube 17 and a one-way valve 18 into the chamber 9. The valve 18 is the same as the one-way valve described in detail in U.S. Pat. No. 7,357,781. As shown in FIG. 2 the neck 20 of the syringe 12 can be connected directly to an inlet 21 integral with the injector barrel 2.

Injection is effected using compressed gas when a trigger 23 is squeezed. The trigger 23 is pivotally mounted on a sleeve 24 inside a trigger guard 25. The compressed gas enters the injector via a hose 26 and a connector 27. When the trigger is squeezed, the plunger 10 moves forwardly to discharge liquid from the passage via a valve 29 of the type described in U.S. Pat. No. 7,357,781, the holder 1 and the nozzle 3. For shallow injections, a generally hemispherical plastic spacer 30 (FIGS. 4 to 6) is mounted on the outer end 32 of the nozzle 3 to reduce the force of liquid entering an injection site. A tapering sleeve 33 in the spacer 30 receives the end 32 of the nozzle 3 in a friction fit. The spacer 30 creates a space between the discharge end of the nozzle 3 and the injection site, i.e. there is a gap between the outer end of the sleeve 33 and the outlet end of the nozzle 3 when the spacer is mounted on the nozzle.

Referring to FIGS. 3, 4 and 7 to 10, the holder 1 includes a tubular body 35 with a central, longitudinally extending passage 36 therethrough. When the holder 1 is slid into the barrel 2 an outwardly extending, annular flange 37 proximate the center of the body 35 abuts the end of the barrel 2 to limit movement of the holder into the barrel. A finger 38 on the discharge end of the barrel 2 mates with a notch 39 in the flange 37 to prevent rotation of the holder in the barrel. An O-ring 41 seals the holder 1 in the barrel 2. Fluid passing through the valve 29 enters the passage 36 in the holder 1 via diametrically opposed holes 42 and is discharged through a small orifice 43 in the tapered outer end 44 (FIGS. 7 and 10) of a cylindrical nozzle 45 at the discharge end of the body 35. Threads 46 are provided near the outer end of the nozzle 45. A cylindrical sleeve 48 extends outwardly around the inner end of the nozzle 45. Diametrically opposed notches 50 (FIG. 7) are provided in the outer free end of the sleeve 48. Each notch 50 includes one more or less radially extending, straight side 51 and one beveled side defining a knife edge 52. As will become apparent from the following description, the knife edge 52 can be replaced by a straight edge similar to the edge 51.

The disposable nozzle 3 is defined by an elongated tubular body 55 with a cylindrical rear end 56 (FIGS. 4 and 9 to 11). The body 55 tapers forwardly from the cylindrical rear end 56 to a small diameter ejection end 57. Three deep concave grooves 59 in the body 55 alternating with longitudinally extending ridges 60 facilitate manual manipulation of the nozzle 3.

Figure 12:
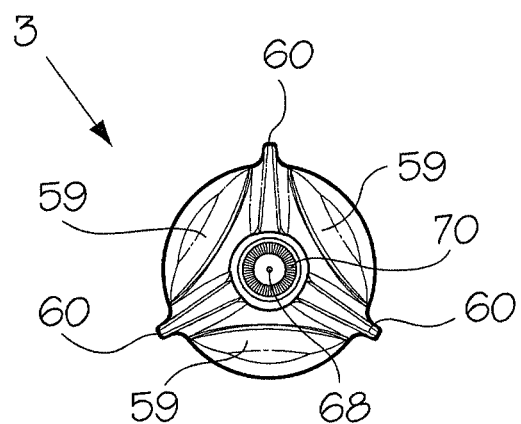
FIG. 12 is a front view of the nozzle.
Figure 13:
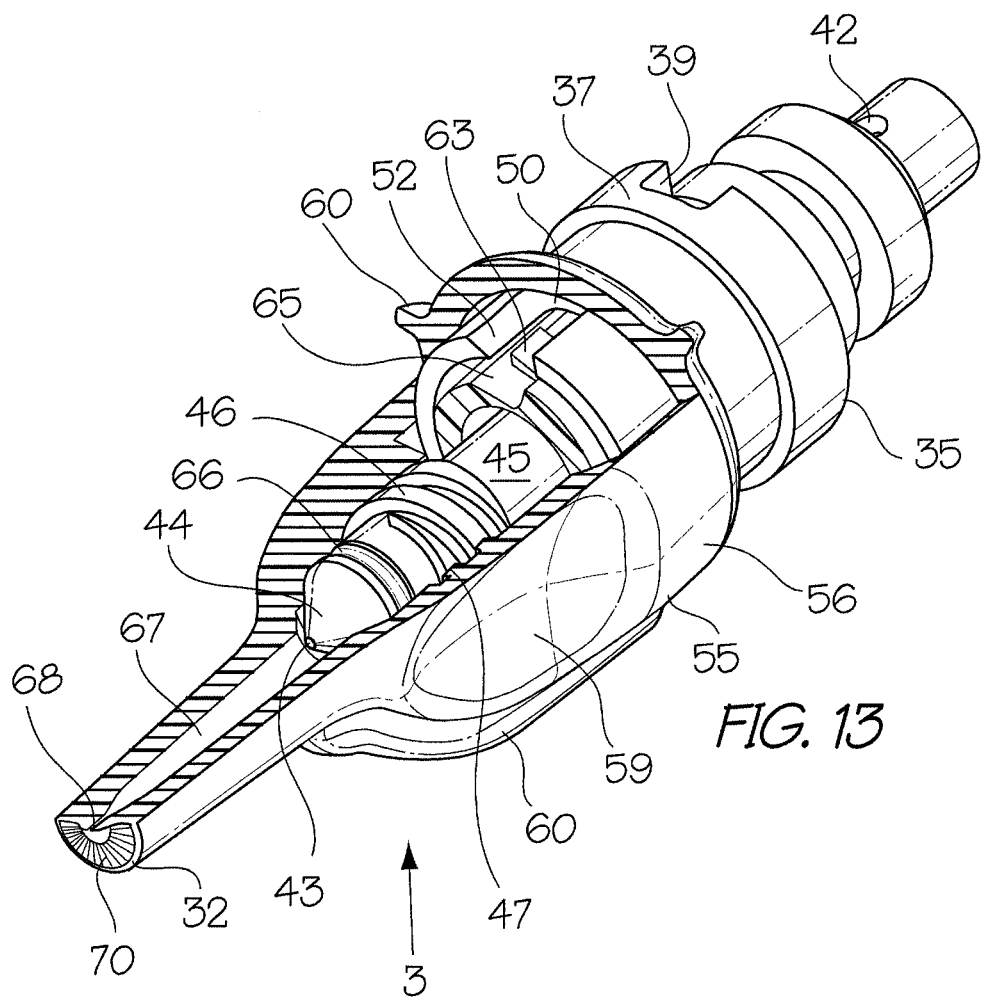
FIG. 13 is a partly sectioned isometric view of the assembled nozzle and holder.
Figure 14:
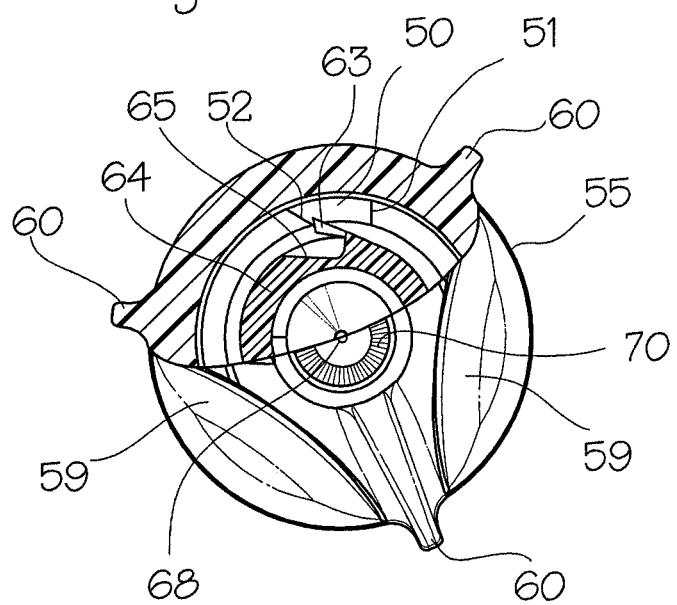
FIG. 14 is a partly sectioned front view of the assembled nozzle and holder.

An annular recess 62 of the rear end 56 in the body 55 receives the holder sleeve 48. A detent or finger 63 extends outwardly at an acute angle from the inner wall 64 of the recess 62. A longitudinally extending groove 65 in the inner wall 64 permits full flexing of the detent 63. When the nozzle 3 is being screwed onto the holder 1 (by rotating the nozzle clockwise in FIGS. 12 and 14), the detent 63 enters one of the notches 50. During each half rotation of the nozzle 3, the detent 63 engages the edge 51 of a notch 50 and flexes into the groove 65. As best shown in FIG. 14, when the nozzle 3 is fully on the holder 1, the detent extends into one of the notches 50. The nozzle 3 is sealed on the holder 1 by an O-ring 66.

Thus, during mounting of the disposable nozzle on the holder 1, the detent 63 repeatedly enters the notches 50 and is deflected inwardly. Contact of the detent 63 with the edges 51 of the notches 50 results in a sound, i.e. an audible signal indicating that the disposable nozzle 3 has not been previously used. In the absence of the detent 63, there would be no resistance to rotation or sound when the disposable nozzle 3 is being mounted on the holder 1, indicating that the disposable nozzle 3 has already been used.

Fluid ejected from the holder 1 passes through a tapering passage 67 and is discharged through a narrow injection orifice 68. Alternating, radially extending ridges and grooves 70 on the discharge end of the nozzle body 55 grip the area around an injection site. Upon completion of each injection, the nozzle 3 is gripped between a thumb and index finger and rotated sharply in a counterclockwise direction. The detent 63, which extends into one of the notches 50, engages the knife edge 52. Continued rotation of the nozzle 3 in the same direction causes the detent 63 to break at its thinner end, i.e. the end attached to the remainder of the nozzle 3. The detent 63 remains in the notch 50 and when the nozzle 3 is removed, the detent falls out of the notch.

In accordance with another aspect, the invention relates to a device for cleaning the holder as described above. With reference to FIGS. 15 to 21, the cleaning device includes a tube 72 and a cap 73 for holding the tube in the discharge end of the injector barrel 2. In order to clean a nozzle holder 1, the holder is removed from the injector barrel and the tube 72 is inserted into the barrel 2 a distance sufficient to engage the valve 29. The tube 72 includes a cylindrical body 75 and an O-ring 76 proximate one end 77 (FIG. 16) thereof for sealing the tube in the barrel 2. Radially extending grooves 78 in the end 77 of the tube 72 permit the flow of fluid from the barrel passage 9 into a central passage 80 in the body 75. The central passage 80 has a narrow diameter end 81 at the barrel end 77 of the body 75 and a wide diameter end 82 for receiving the nozzle 45 of the holder 1 (FIGS. 15, 20 and 21). When the holder 1 is inserted into the tube 72, the conical end 44 of the holder engages a conical shoulder 84 between the narrow and wide diameter portions of the passage 80.

With the holder 1 and the tube 72 in the injector barrel 2, and the cap 73 is attached to the barrel to retain the holder 1 and the tube 72 in position. For such purpose, the cap 73 is defined by a tubular body 86, one end 87 of which is internally threaded for engaging the externally threaded discharge end of the injector barrel 2. Longitudinally extending ribs 88 are provided on the end 87 of the body 86 facilitating manual manipulation of the cap 73. An annular inwardly extending flange 89 on the other end 90 of the body 86 engages a beveled shoulder 92 (FIGS. 15 and 20) on the holder 1.

A third aspect of the present invention is an adapter indicated generally at 94 in FIGS. 22 and 23 for connecting the internally threaded neck 20 of a syringe 12 to the cap 95 of a medicine bottle 96. The cap 95 and the bottle 96 are conventional items, the cap 95 including a metal body 98 with a puncturable membrane 99 in the top center thereof. The adapter 94 includes a cylindrical skirt 101 with a plurality of longitudinally extending notches 102 extending substantially the entire length thereof to divide the skirt into resilient fingers 103. Each finger 103 has an interior bead or flange 105 on the bottom end thereof for engaging the bottom of the cap 95 to retain the adapter on the bottle and cap. When placing the adapter on the bottle cap 95, it is merely necessary to exert a downward pressure on the adapter to flex the fingers 103 outwardly. Pulling upwardly on the adapter releases the beads 105 from the bottom of the cap 95. An externally threaded neck 106 extends upwardly from the top center of a circular top 107 on the skirt 101 for mating with the internally threaded neck 20 of a syringe 12. Triangular reinforcing gussets 108 extend between the neck 106 and the top 107 of the cap. A passage 109 extends downwardly through the neck 106 and a needle 111, whereby fluid can be drawn from the bottle 96 into the syringe 12.

The invention claimed is:

1. A nozzle assembly for use on a discharge end of a barrel of a needleless injector comprising a holder for mounting in the discharge end of the barrel and a disposable nozzle for mounting on the holder, The holder including:
   a tubular holder body having a central, longitudinally extending passage therethrough permitting a passage of fluid from the injector barrel to the disposable nozzle;
   an externally threaded holder nozzle at a front, discharge end of the holder body;
   a cylindrical sleeve on the holder body around a rear end of said externally threaded holder nozzle; and
   at least one first notch in a front, free end of the sleeve;
the disposable nozzle including:
   a tubular, internally threaded nozzle body for mounting the disposable nozzle on the front end of the holder;
   an annular recess with inner and outer walls in a rear end of the nozzle body for receiving the sleeve of the holder when the disposable nozzle is mounted on the holder, and
   a resilient, frangible detent extending outwardly at an acute angle from said inner wall of said recess into a path of travel of the holder sleeve when the disposable nozzle is being threaded onto the holder,
   whereby, when the disposable nozzle is rotated in one direction while being threaded onto the holder, the detent is deflected towards said inner wall of the recess, and when the disposable nozzle is fully on the holder, the detent extends into the at least one first notch and reverse rotation of the disposable nozzle results in breaking of the detent.

2. The nozzle assembly of claim 1, wherein said disposable nozzle body includes an outer surface, concave grooves in said outer surface, and longitudinally extending ridges alternating with said grooves for facilitating manual manipulation of the disposable nozzle.

3. The nozzle assembly of claim 1 including an annular flange extending outwardly from said holder body; an internally threaded cap for mounting on an externally threaded discharge end of the injector barrel, and an inwardly extending annular flange on an outer end of said cap for retaining the holder in the barrel.

4. The nozzle assembly of claim 1, including a longitudinally extending groove in said inner wall of the annular recess for receiving the detent following separation of the detent from the inner wall of said recess.

5. The nozzle assembly of claim 1 including a pair of diametrically opposed first notches in the front end of the holder sleeve.

6. The nozzle assembly of claim 5, wherein each first notch includes a radially extending straight side and a knife edge for facilitating breaking of the detent when the disposable nozzle is rotated during removal from the holder.

7. The nozzle assembly of claim 6 including a second notch in a rear end of an annular flange on the holder body for mating with a finger on the discharge end of the injector barrel to prevent rotation of the holder relative to the injector barrel.

\* \* \* \* \*